(12) United States Patent
Ding

(10) Patent No.: US 11,020,544 B2
(45) Date of Patent: Jun. 1, 2021

(54) COMPOSITE HEATING TYPE FLUE-CURING DEVICE AND COMPOSITE HEATING METHOD FOR CIGARETTES

(71) Applicant: Shenzhen Jianan Technology Co., Limited, Guangdong (CN)

(72) Inventor: Jianjun Ding, Guangdong (CN)

(73) Assignee: SHENZHEN JIANAN TECHNOLOGY CO., LIMITED, Shenzhen (CN)

( * ) Notice: Subject to any disclaimer, the term of this patent is extended or adjusted under 35 U.S.C. 154(b) by 323 days.

(21) Appl. No.: 16/093,966

(22) PCT Filed: Dec. 29, 2017

(86) PCT No.: PCT/CN2017/120144
§ 371 (c)(1),
(2) Date: Oct. 15, 2018

(87) PCT Pub. No.: WO2019/127472
PCT Pub. Date: Jul. 4, 2019

(65) Prior Publication Data
US 2020/0345959 A1    Nov. 5, 2020

(51) Int. Cl.
*A61M 11/04* (2006.01)
*A61M 15/06* (2006.01)
*A24F 40/46* (2020.01)
*H05B 1/02* (2006.01)
*A24F 40/20* (2020.01)
*A24F 40/50* (2020.01)

(52) U.S. Cl.
CPC .......... *A61M 11/042* (2014.02); *A24F 40/46* (2020.01); *A61M 15/06* (2013.01); *A24F 40/20* (2020.01); *A24F 40/50* (2020.01); *H05B 1/0244* (2013.01); *H05B 2203/021* (2013.01)

(58) Field of Classification Search
CPC ....... A61M 11/042; A61M 15/06; A24F 40/46
USPC .......................................... 131/329
See application file for complete search history.

(56) References Cited

U.S. PATENT DOCUMENTS 5,726,421 A * 3/1998 Fleischhauer ......... A24F 47/008
219/260
5,878,752 A * 3/1999 Adams .................. A24F 47/008
131/329

(Continued)

FOREIGN PATENT DOCUMENTS

CN    202907797 U    5/2013
CN    205161888 U    4/2016

*Primary Examiner* — Alexander Gilman

(57) ABSTRACT

A flue-curing device comprises a case, one end of the case is provided with an opening, and a fixing barrel communicated with the opening is defined an inner portion of the case, the fixing barrel is sequentially provided with a heating chamber and an airflow heating pipe; the airflow heating pipe is sleeved by a heat generating assembly configured to heat air that is to flow to the cigarette and to transfer heat to the heating chamber to heat the cigarette; or the airflow heating pipe and the heating chamber are both sleeved by the heat generating assembly configured to simultaneously heat the heating chamber and the airflow heating pipe to achieve a composite heating of the cigarette. The present application can solve the problem that the cigarette evaporation is insufficient or the evaporation is too fast, and satisfy a habit of a user to smoke for a long time.

10 Claims, 8 Drawing Sheets

(56) References Cited

U.S. PATENT DOCUMENTS

| | | | | |
|---|---|---|---|---|
| 5,954,979 | A * | 9/1999 | Counts | A24F 47/008 |
| | | | | 131/194 |
| 9,913,493 | B2 * | 3/2018 | Worm | A24F 15/01 |
| 10,051,894 | B2 * | 8/2018 | Gavrielov | A24F 40/70 |
| 10,165,797 | B2 * | 1/2019 | Chen | A24F 47/008 |
| 10,827,782 | B2 * | 11/2020 | Fernando | A24F 40/51 |
| 2002/0005207 | A1 * | 1/2002 | Wrenn | A24C 5/478 |
| | | | | 131/194 |
| 2004/0089314 | A1 * | 5/2004 | Felter | A24F 47/008 |
| | | | | 131/194 |
| 2012/0060853 | A1 * | 3/2012 | Robinson | H05B 3/42 |
| | | | | 131/191 |
| 2012/0234821 | A1 * | 9/2012 | Shimizu | A24F 13/00 |
| | | | | 219/227 |
| 2015/0196059 | A1 * | 7/2015 | Liu | H05B 3/06 |
| | | | | 131/329 |
| 2015/0313284 | A1 * | 11/2015 | Liu | A24F 40/40 |
| | | | | 131/329 |
| 2016/0007651 | A1 * | 1/2016 | Ampolini | A24F 47/008 |
| | | | | 131/328 |
| 2016/0066621 | A1 * | 3/2016 | DePiano | A24F 47/008 |
| | | | | 131/328 |
| 2016/0095357 | A1 * | 4/2016 | Burton | B23P 19/00 |
| | | | | 131/328 |
| 2016/0113326 | A1 * | 4/2016 | Li | H05B 3/00 |
| | | | | 131/329 |
| 2016/0262455 | A1 * | 9/2016 | Chen | A24F 47/008 |

* cited by examiner

COMPOSITE HEATING TYPE FLUE-CURING DEVICE AND COMPOSITE HEATING METHOD FOR CIGARETTES

FIELD OF THE PRESENT APPLICATION

The present application relates to a field of electronic cigarette devices, and more particularly relates to a composite heating type flue-curing device and a composite heating method for cigarettes.

BACKGROUND OF THE PRESENT APPLICATION

Traditional smoking is finished by igniting tobacco with a flame to produce smoke for smokers to smoke. The smoke produced by burning of tobacco usually contains a variety of harmful substances. Therefore, traditional tobacco not only causes serious respiratory diseases to smokers, but also easily causes second-hand smoke hazards.

At present, cigarette flue-curing devices are commercially available, one kind of the cigarette flue-curing devices is annular heating on sides of a cigarette, another one kind of the cigarette flue-curing devices is air heating, the annular heating does not sufficiently heat an upper end and a lower end of the cigarette, and the taste is not soft. The air heating is to heat cold air to heat the cigarette, although the heating is sufficient, the nicotine in the cigarette is easily evaporated, hence it is difficult to satisfy a user's habit of smoking a cigarette for a long time.

Therefore, how to let the user experience the taste of real cigarettes, and at the same time solve the defects that an existing flue-curing device is insufficiently evaporated or evaporated too fast is an urgent problem to be solved for a current flue-curing device.

SUMMARY OF THE PRESENT APPLICATION

Technical problems to be solved in the present application is to provide a composite heating type flue-curing device.

One embodiment of the present application provides a composite heating type flue-curing device comprising a case, one end of the case is provided with an opening, and a fixing barrel communicated with the opening is defined in an inner portion of the case, one end of the fixing barrel which is opposite to the opening is sequentially provided with a heating chamber and an airflow heating pipe which are communicated with each other, and the airflow heating pipe is formed by radially shrinking the heating chamber in a direction opposite to the opening;

One end of a cigarette is sequentially inserted into the fixing barrel and the heating chamber along the opening and is abutted against an end wall of one end of the heating chamber which is opposite to the opening, the other end of the cigarette extends outside the case from the opening for a user to inhale; and The airflow heating pipe is sleeved by a heat generating assembly, the heat generating assembly is configured to heat air that is to flow to the cigarette from an inner portion of the airflow heating pipe, and to simultaneously transfer heat to the heating chamber to heat an outer peripheral wall of the cigarette; or the airflow heating pipe and the heating chamber are both sleeved by the heat generating assembly, the heat generating assembly is configured to simultaneously heat the heating chamber and the airflow heating pipe to achieve a composite heating of the cigarette.

Typically, the heating chamber comprises a first heating barrel and at least one second heating barrel defined between the first heating barrel and the fixing barrel, the airflow heating pipe is formed by radially shrinking the first heating barrel in a direction opposite to the opening; and The heating chamber further comprises a first connecting barrel connected between the first heating barrel and the second heating barrel, and a second connecting barrel connected between the second heating barrel and the fixing barrel.

Typically, the first heating barrel is defined on an inner peripheral wall of one end of a first limiting step near the second heating barrel, a second limiting step is defined on an inner peripheral wall of one end of the second heating barrel near the first heating barrel, and outer walls of two ends of the first connecting barrel are abutted against the first limiting step and the second limiting step to space and connect the first heating barrel and the second heating barrel.

Typically, the heat generating assembly comprises a first heat generating member sleeved outside the airflow heating pipe and a second heat generating member sleeved outside the second heating barrel; and The first heat generating member is configured to heat air inside the airflow heating pipe that is to flow to the cigarette, and to simultaneously transfer heat to the first heating barrel to heat a portion of the outer peripheral wall of the cigarette, and the second heat generating member is configured to heat the second heating barrel to heat another portion of the outer peripheral wall of the cigarette, so as to achieve a composite multi-stage heating of the cigarette.

Typically, the heating chamber comprises a first heating barrel and a second connecting barrel which is defined between the first heating barrel and the fixing barrel, the airflow heating pipe is formed by radially shrinking the first heating barrel in a direction opposite to the opening.

Typically, the heat generating assembly comprises a first heat generating member sleeved outside the airflow heating pipe; and the first heat generating member is configured to heat air inside the airflow heating pipe that is to flow to the cigarette, and to simultaneously transfer heat to the first heating barrel to heat a portion of the outer peripheral wall of the cigarette, so as to achieve a composite heating of the cigarette.

Typically, the heat generating assembly comprises a first heat generating member sleeved outside the airflow heating pipe, and a second heat generating member sleeved outside the first heating barrel; and The first heat generating member is configured to heat air inside the airflow heating pipe that is to flow to the cigarette, and the second heat generating member is configured to directly heat the first heating barrel to heat another portion of the outer peripheral wall of the cigarette, so as to achieve a composite heating of the cigarette.

Typically, a first thermal insulating barrel is sleeved outside the first heat generating member at a space, a first fixing bracket is sleeved on an outer wall of one end of the fixing barrel near the heating chamber, and the first fixing bracket partially extends toward the heating chamber to form a plurality of first clamping arms, a second thermal insulating barrel is clamped in the plurality of first clamping arms, so that the second thermal insulating barrel is sleeved outside the heat generating assembly, the heating chamber and the first thermal insulating barrel with a space;

A second fixing bracket is defined at one end of the second thermal insulating barrel opposite to the first fixing bracket, and the second fixing bracket partially extends toward the heating chamber to form a plurality of second clamping arms, the plurality of the second clamping arm clamp on an outer wall of one end of the second insulating barrel opposite to the first fixing bracket; and One end of the first thermal insulating barrel abuts against an outer end wall of the heating chamber which is opposite to the opening, and the other end of the first thermal insulating barrel abuts against an inner end wall of the second fixing bracket, the inner end wall of the second fixing bracket faces the opening.

Typically, the second fixing bracket is provided with a through hole at a center of the second fixing bracket, and an air intake pipe passes through the through hole to connect to the airflow heating pipe; and A first thermal insulating space is formed between the first thermal insulating barrel and the first heat generating element; the first fixing bracket, the second thermal insulating barrel and the second fixing bracket are enclosed to form a thermal insulating case; a second insulated space is formed among the heat generating assembly, the heating chamber and the first thermal insulating barrel which are defined in the thermal insulating case.

Typically, a bottom cover is detachably provided at one end of the case opposite to the opening, and a first air inlet hole is defined on the bottom cover to allow air to enter an inner portion of the case; and A fixing member is defined between the bottom cover and the second fixing bracket, and the fixing member is provided with a second air inlet hole, and an end of the air intake pipe opposite to the opening extends outside the through hole and is inserted into the second air inlet hole, the first air inlet hole, the second air inlet hole, the air intake pipe and the airflow heating pipe are sequentially communicated to form an air intake passage.

Typically, the airflow heating pipe and the first heating pipe are both made of a thermal conduction material; the second connecting pipe, the first insulating barrel, the second insulating barrel, the first fixing bracket, the second fixing bracket, and the fixing barrel are all made of a thermal insulation material.

The present application further provides a composite heating method using the composite heating type flue-curing device, comprising following steps:

S1. inserting a cigarette sequentially into the fixing barrel and the heating chamber along the opening and is abutted against an end wall of one end of the heating chamber opposite to the opening;

S2. controlling the second heat generating member to heat the second heating barrel to heat a portion of the cigarette;

S3. controlling the first heat generating member to heat the airflow heating pipe, so as to heat air that is to flow to the cigarette, and to simultaneously transfer heat of the airflow heating pipe to the first heating barrel to heat another portion of the cigarette, so as to achieve the composite multi-stage heating of the cigarette.

The present application further provides composite heating method using the composite heating type flue-curing device, comprising following steps:

S1. a cigarette is sequentially inserted into the fixing barrel and the heating chamber along the opening and is abutted against an end wall of one end of the heating chamber opposite to the opening;

S2. controlling the first heat generating member to heat the airflow heating pipe, so as to heat air that is to flow to the cigarette, and to simultaneously transfer heat of the airflow heating pipe to the first heating barrel to achieve the composite heating of the cigarette.

The present application further provides a composite heating method using the composite heating type flue-curing device, comprising following steps:

S1. a cigarette is sequentially inserted into the fixing barrel and the heating chamber along the opening and is abutted against an end wall of one end of the heating chamber opposite to the opening;

S2. controlling the second heat generating member to heat the first heating barrel to heat the cigarette;

S3. controlling the first heat generating member to heat the airflow heating pipe, so as to heat air that is to flow to the cigarette to achieve the composite heating of the cigarette.

One or more technical solutions provided in the embodiments of the present application have at least the following technical effects or advantages: solving the problem that the cigarette is insufficiently evaporated and evaporating too fast, and satisfying a habit of a user to smoke for a long time.

BRIEF DESCRIPTION OF THE DRAWINGS

In order to more clearly illustrate the embodiments of the present application or the technical solutions in the prior art, the drawings used in the embodiments or the description of the prior art will be briefly described below. Obviously, the drawings in the following description are only It is an embodiment of the present application, and those skilled in the art can obtain other drawings according to the provided drawings without any creative work.

DETAILED DESCRIPTION OF THE PREFERRED EMBODIMENT

The embodiment of the present application provides a composite heating type flue-curing device. The specific idea is as follows: the flue-curing device comprises a case, one end of the case is provided with an opening, and a fixing barrel communicated with the opening is defined an inner portion of the case, one end of the fixing barrel which is opposite to the opening is sequentially provided with a heating chamber and an airflow heating pipe which are communicated with each other, and the airflow heating pipe is formed by radially shrinking the heating chamber in a direction opposite to the opening; one end of a cigarette is sequentially inserted into the fixing barrel and the heating chamber along the opening and is abutted against an end wall of one end of the heating chamber which is opposite to the opening, the other end of the cigarette extends outside the case from the opening for the user to inhale; the airflow heating pipe is sleeved by a heat generating assembly, the heat generating assembly is configured to heat air that is to flow to the cigarette from an inner portion of the airflow heating pipe, and to simultaneously transfer heat to the heating chamber to heat an outer peripheral wall of the cigarette; or the airflow heating pipe and the heating chamber are both sleeved by the heat generating assembly, the heat generating assembly is configured to simultaneously heat the heating chamber and the airflow heating pipe to achieve a composite heating of the cigarette. The composite heating type flue-curing device provided by the present application can solve the problem that the cigarette evaporation is insufficient or the evaporation is too fast, and satisfy a habit of a user to smoke for a long time.

For well understanding of the above technical solutions, the above technical solutions will be described in detail in conjunction with the drawings and typical embodiments. It should be understood that embodiments and specific features of the embodiments of the present application are detailed descriptions to the technical solutions of the present application, rather than limitations of the technical solutions of the present application. In case of no conflicts, the embodiments and specific features of the embodiments of the present application may be combined with each other.

First Embodiment

Figure 1:
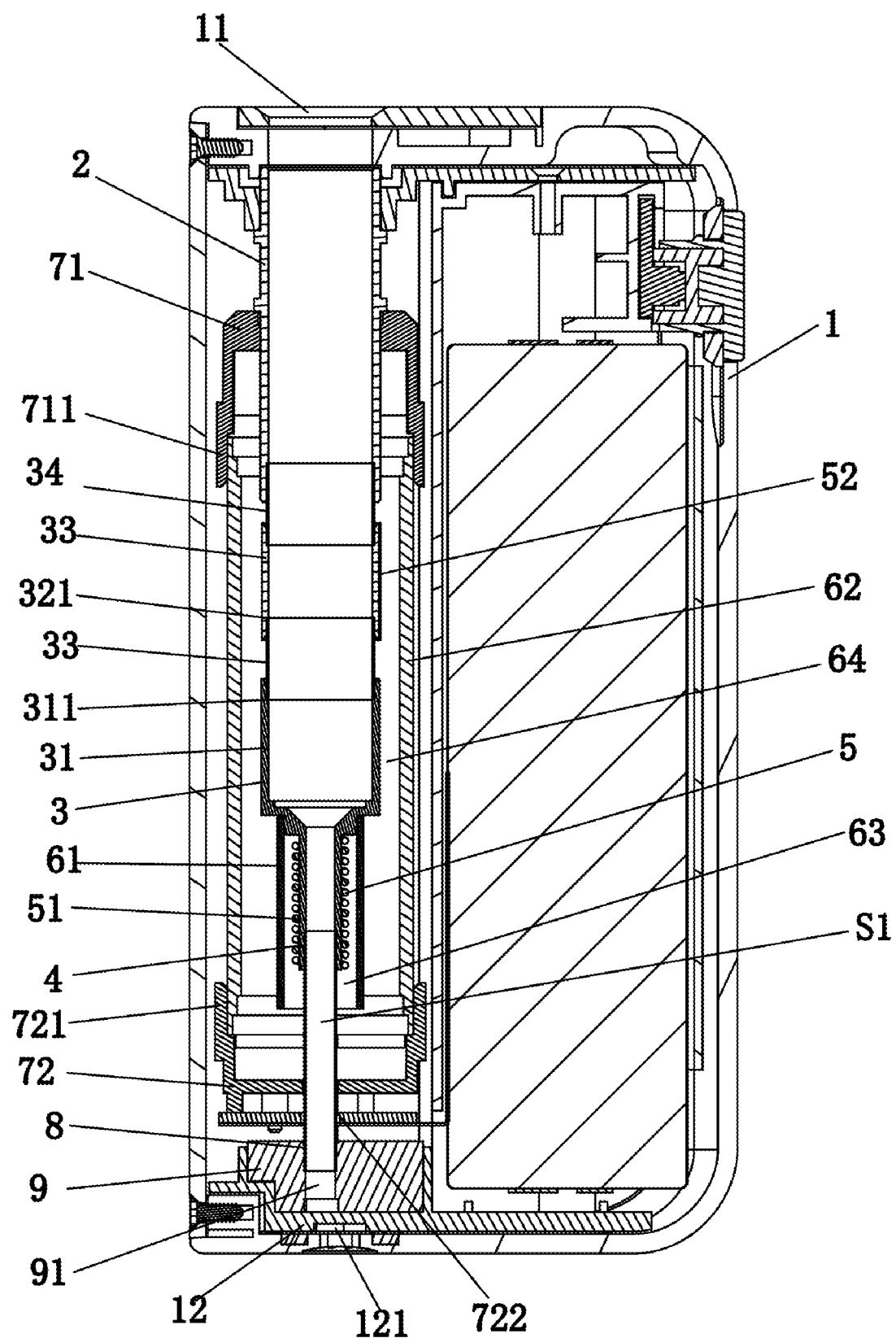
FIG. 1 is a cross-sectional view of a composite heating type flue-curing device provided by a first embodiment of the present application.

FIG. 1 is a cross-sectional view of a composite heating type flue-curing device provided by a first embodiment of the present application.

As shown in FIG. 1, the embodiment of the present application provides a composite heating type flue-curing device comprising a case 1, one end of the case 1 is provided with an opening 11, and a fixing barrel 2 communicated with the opening 11 is defined in an inner portion of the case 1, one end of the fixing barrel 2 which is opposite to the opening 11 is sequentially provided with a heating chamber 3 and an airflow heating pipe 4 which are communicated with each other, and the airflow heating pipe 4 is formed by radially shrinking the heating chamber 3 in a direction opposite to the opening 11; one end of a cigarette is sequentially inserted into the fixing barrel 2 and the heating chamber 3 along the opening 11 and is abutted against an end wall of one end of the heating chamber 3 which is opposite to the opening 11, the other end of the cigarette extends outside the case 1 from the opening 11 for a user to inhale; the airflow heating pipe 4 is sleeved by a heat generating assembly 5, the heat generating assembly 5 is configured to heat air that is to flow to the cigarette from an inner portion of the airflow heating pipe 4, and to simultaneously transfer heat to the heating chamber 3 to heat an outer peripheral wall of the cigarette; or the airflow heating pipe 4 and the heating chamber 3 are both sleeved by the heat generating assembly 5, the heat generating assembly 5 is configured to simultaneously heat the heating chamber 3 and the airflow heating pipe 4 to achieve a composite heating of the cigarette.

In the present embodiment, the heating chamber 3 comprises a first heating barrel 31 and at least one second heating barrel 32 defined between the first heating barrel 31 and the fixing barrel 2, the airflow heating pipe 4 is formed by radially shrinking the first heating barrel 31 in a direction opposite to the opening 11; the heating chamber 3 further comprises a first connecting barrel 33 connected between the first heating barrel 31 and the second heating barrel 32, and a second connecting barrel 34 connected between the second heating barrel 32 and the fixing barrel 2. In other embodiments, a plurality of second heating barrels 32 may also be defined to more fully heat the cigarette.

Figure 2:
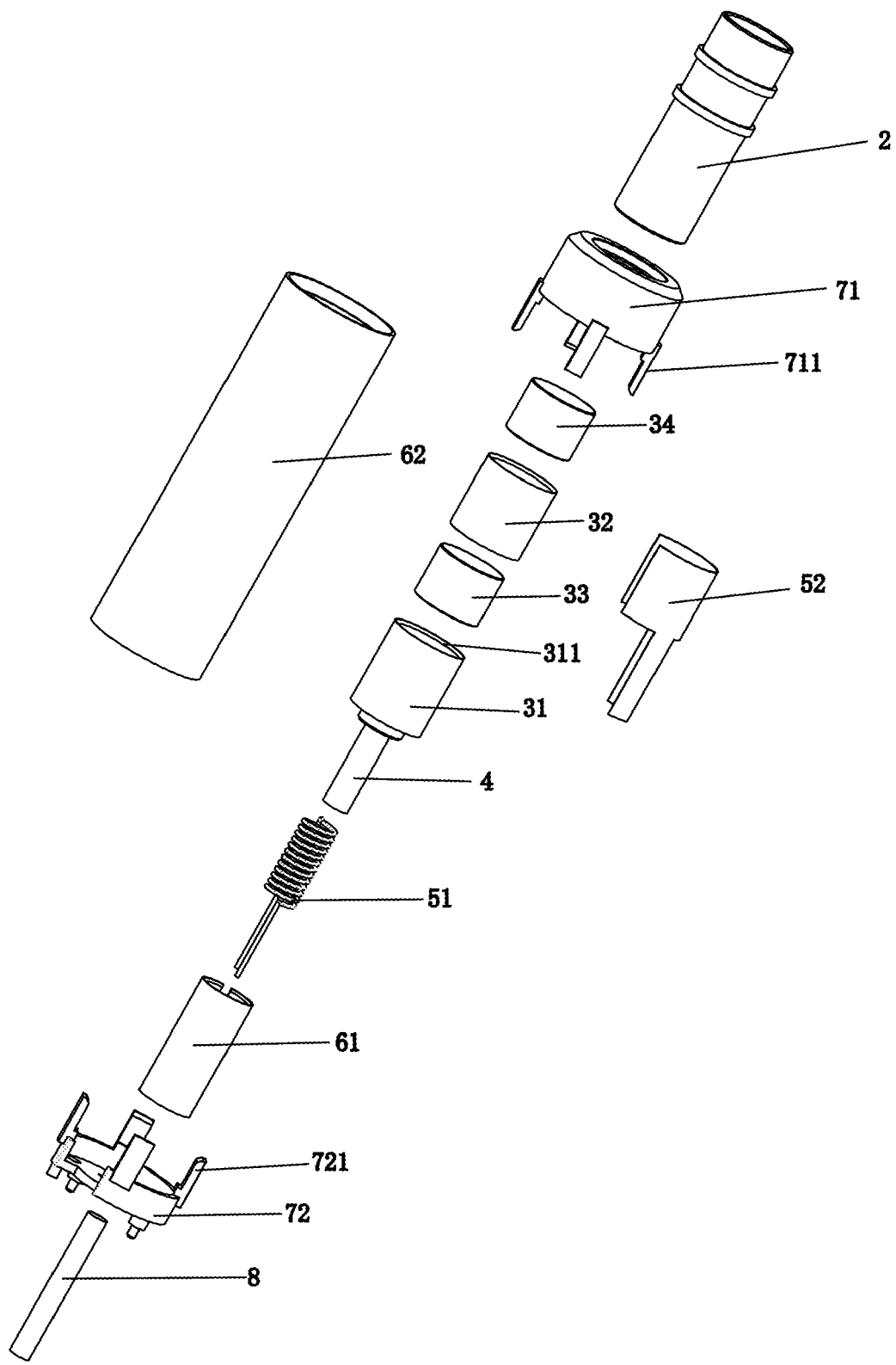
FIG. 2 is a partial structural view of a composite heating type flue-curing device provided by a first embodiment of the present application.

As shown in FIG. 1 and FIG. 2, due to a segmental heating of the cigarette, the first heating barrel 31 is defined on an inner peripheral wall of one end of a first limiting step 311 near the second heating barrel 32, a second limiting step 321 is defined on an inner peripheral wall of one end of the second heating barrel 32 near the first heating barrel 31, and outer walls of two ends of the first connecting barrel 33 are abutted against the first limiting step 311 and the second limiting step 321 to space and connect the first heating barrel 31 and the second heating barrel 32.

In the present embodiment, the heat generating assembly 5 comprises a first heat generating member 51 sleeved outside the airflow heating pipe 4 and a second heat generating member 52 sleeved outside the second heating barrel 32; the first heat generating member 51 is configured to heat air inside the airflow heating pipe 4 that is to flow to the cigarette, and to simultaneously transfer heat to the first heating barrel 31 to heat a portion of the outer peripheral wall of the cigarette, and the second heat generating member 52 is configured to heat the second heating barrel 32 to heat another portion of the outer peripheral wall of the cigarette, so as to achieve a composite multi-stage heating of the cigarette.

Typically, the first heat generating member 51 and the second heat generating assembly 52 may be set to the same temperature or may be set to different temperatures to meet diversified requirements of customers.

In order to thermally insulate the heat generating assembly 5, a first thermal insulating barrel 61 is sleeved outside the first heat generating member 51 at a space, a first fixing bracket 71 is sleeved on an outer wall of one end of the fixing barrel 2 near the heating chamber 3, and the first fixing bracket 71 partially extends toward the heating chamber 3 to form a plurality of first clamping arms 711, a second thermal insulating barrel 62 is clamped in the plurality of first clamping arms 711, so that the second thermal insulating barrel 62 is sleeved outside the heat generating assembly 5, the heating chamber 3 and the first thermal insulating barrel 61 with a space; a second fixing bracket 72 is defined at one end of the second thermal insulating barrel 62 opposite to the first fixing bracket 71, and the second fixing bracket 72 partially extends toward the heating chamber 3 to form a plurality of second clamping arms 721, the plurality of the second clamping arm 721 clamp on an outer wall of one end of the second insulating barrel 62 opposite to the first fixing bracket 71; one end of the first thermal insulating barrel 61 abuts against an outer end wall of the heating chamber 3 which is opposite to the opening 11, and the other end of the first thermal insulating barrel 61 abuts against an inner end wall of the second fixing bracket 72, the inner end wall of the second fixing bracket 72 faces the opening 11.

For further thermal insulation, a first thermal insulating space 63 is formed between the first thermal insulating barrel 61 and the first heat generating element 51; the first fixing bracket 71, the second thermal insulating barrel 62 and the second fixing bracket 72 are enclosed to form a thermal insulating case; a second insulated space 64 is formed among the heat generating assembly 5, the heating chamber 3 and the first thermal insulating barrel 61 which are defined in the thermal insulating case. The second fixing bracket 72 is provided with a through hole 722 at a center of the second fixing bracket 72, and an air intake pipe 8 passes through the through hole 722 to connect to the airflow heating pipe 4.

As shown in FIG. 1, a bottom cover 12 is detachably provided at one end of the case 1 opposite to the opening 11, and a first air inlet hole 121 is defined on the bottom cover 12 to allow air to enter an inner portion of the case 1; a fixing member 9 is defined between the bottom cover 12 and the second fixing bracket 72, and the fixing member 9 is provided with a second air inlet hole 91, an end of the air intake pipe 8 opposite to the opening 11 extends outside the through hole 722 and is inserted into the second air inlet hole 91, the first air inlet hole 121, the second air inlet hole 91, the air intake pipe 8 and the airflow heating pipe 4 are sequentially communicated to form an air intake passage S1.

In this embodiment, the airflow heating pipe 4, the first heating barrel 31 and the first heating barrel 32 are all made of a thermal conduction material; the first connecting pipe 33, the second connecting barrel 34, the first insulating barrel 61, the second insulating barrel 62, the first fixing bracket 71, the second fixing bracket 72, and the fixing barrel 2 are all made of a thermal insulation material. The first heating barrel 31 and the airflow heating pipe 4 are both made of a thermal conduction material, so that heat of the airflow heating pipe 4 can be transferred to the first heating barrel 31 to realize the composite heating of the cigarette.

In this embodiment, the bottom cover 12, the fixing member 9, the second fixing bracket 72, the first thermal insulating barrel 61, the first fixing bracket 71, the fixing barrel 2, the heating chamber 3, and the airflow heating pipe 4 are all detachably connections, so as to easily clean the flue-curing device.

Second Embodiment

Figure 3:
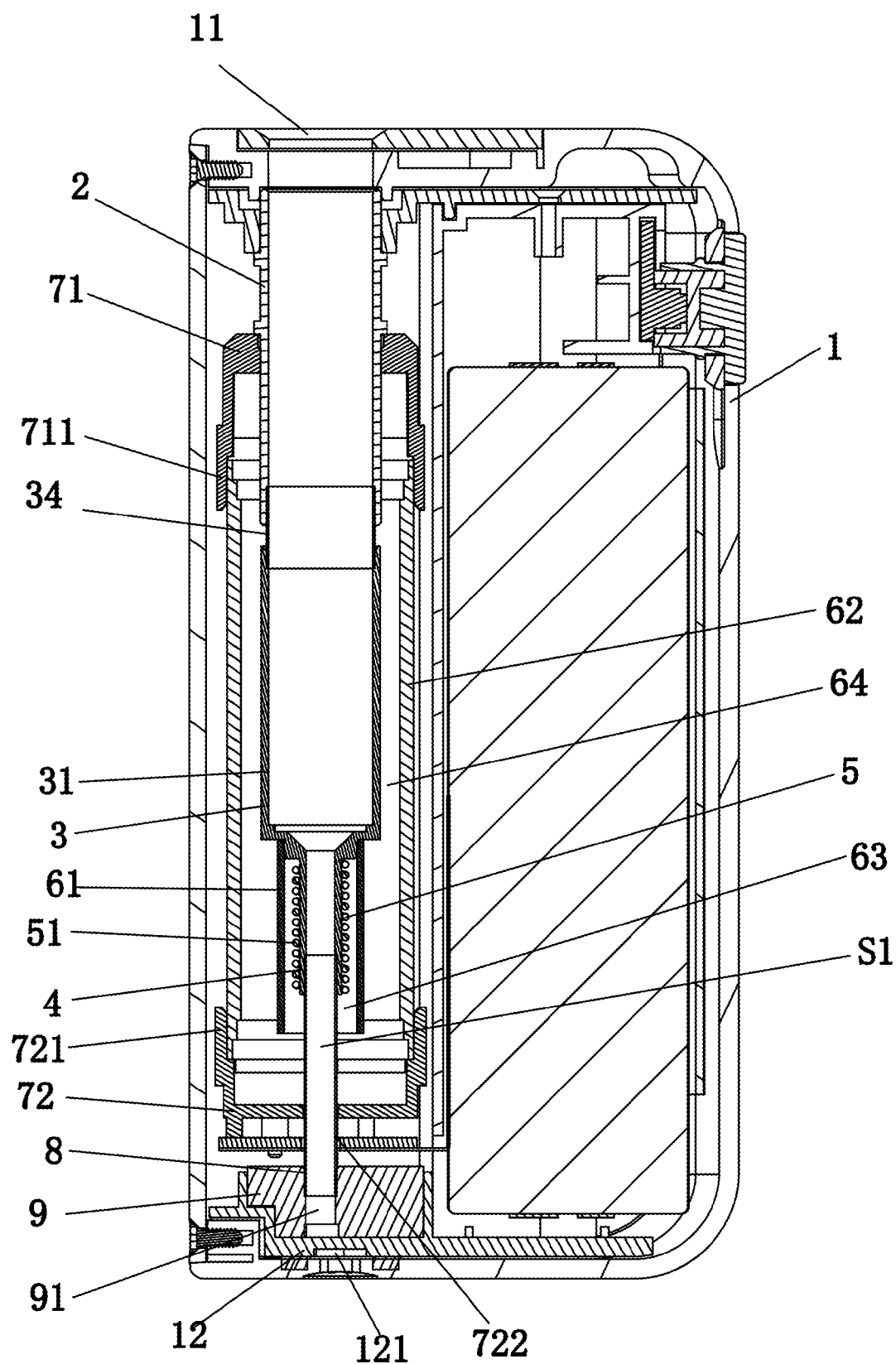
FIG. 3 is a cross-sectional view of a composite heating type flue-curing device provided by a second embodiment of the present application.

As shown in FIG. 3, differences between the present embodiment and the first embodiment is that structures of the heating chamber 3 and the heat generating assembly 5 are different. In the present embodiment, the heating chamber 3 comprises a first heating barrel 31 and a second connecting barrel 34 which is defined between the first heating barrel 31 and the fixing barrel 2, the airflow heating pipe 4 is formed by radially shrinking the first heating barrel 31 in a direction opposite to the opening 11.

Figure 4:
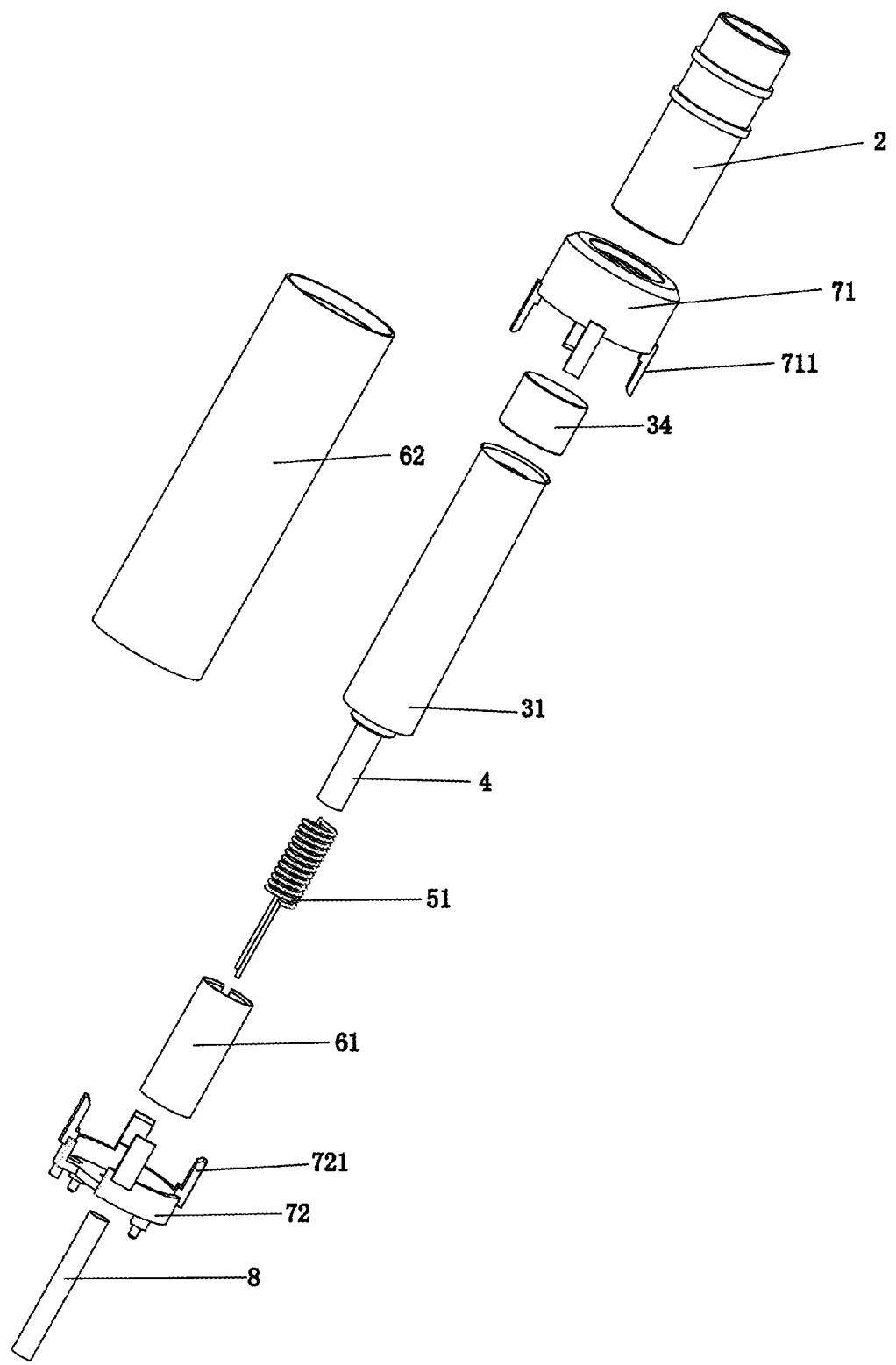
FIG. 4 is a partial structural exploded view of a composite heating type flue-curing device according to a second embodiment of the present application.

As shown in FIG. 3 and FIG. 4, the heat generating assembly 5 comprises a first heat generating member 51 sleeved outside the airflow heating pipe 4; the first heat generating member 51 is configured to heat air inside the airflow heating pipe 4 that is to flow to the cigarette, and to simultaneously transfer heat to the first heating barrel 31 to heat a portion of the outer peripheral wall of the cigarette, so as to achieve a composite heating of the cigarette.

Third Embodiment

Figure 5:
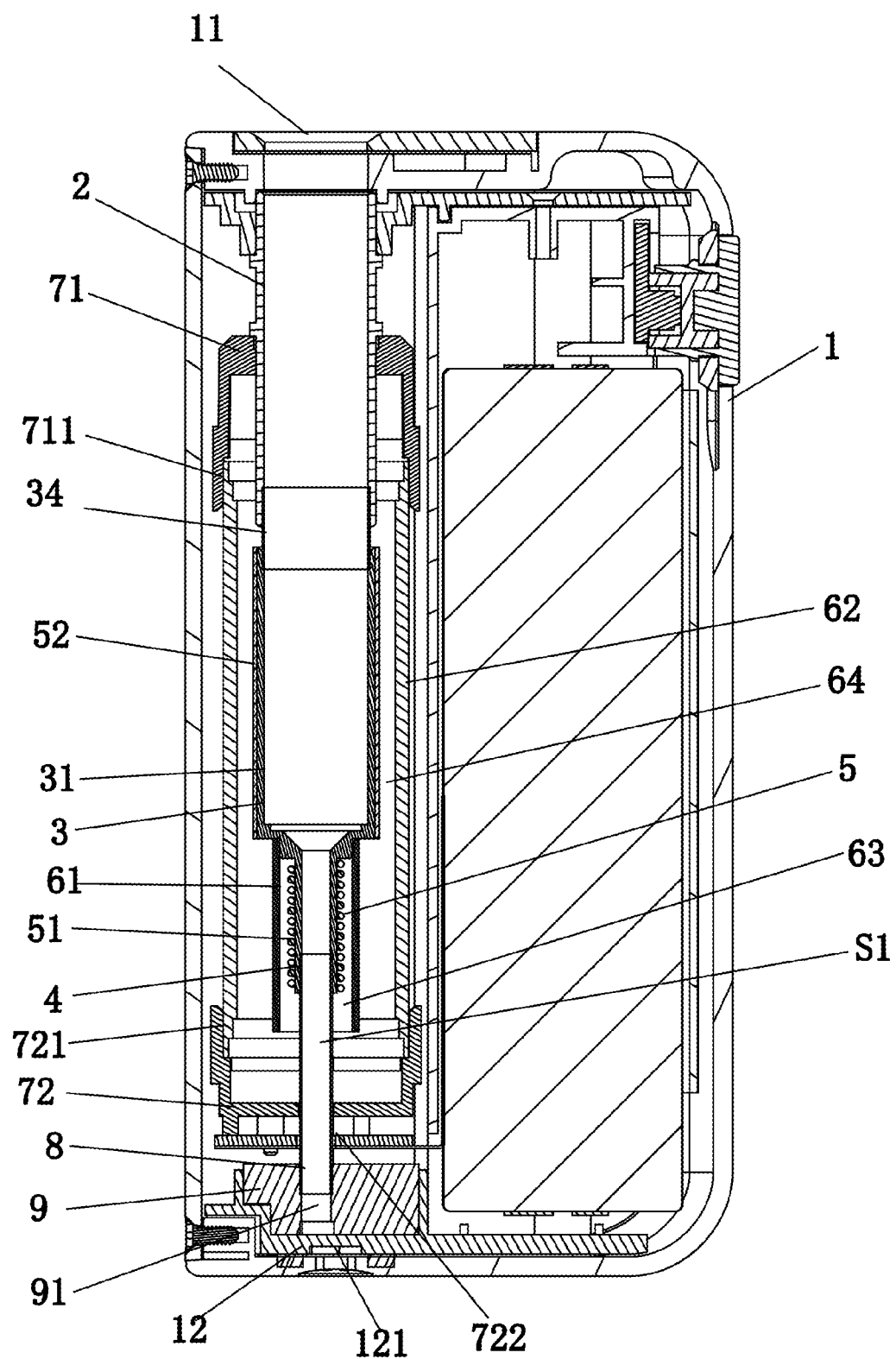
FIG. 5 is a cross-sectional view showing a composite heating type flue-curing device according to a third embodiment of the present application.

As shown in FIG. 5, a difference between the present embodiment and the second embodiment is only that the structure of the heat generating assembly 5. In the present embodiment, the heating chamber 3 is the same as that in the second embodiment, the heating chamber 3 comprises a first heating barrel 31 and a second connecting barrel 34 which is defined between the first heating barrel 31 and the fixing barrel 2, the airflow heating pipe 4 is formed by radially shrinking the first heating barrel 31 in a direction opposite to the opening 11.

Figure 6:
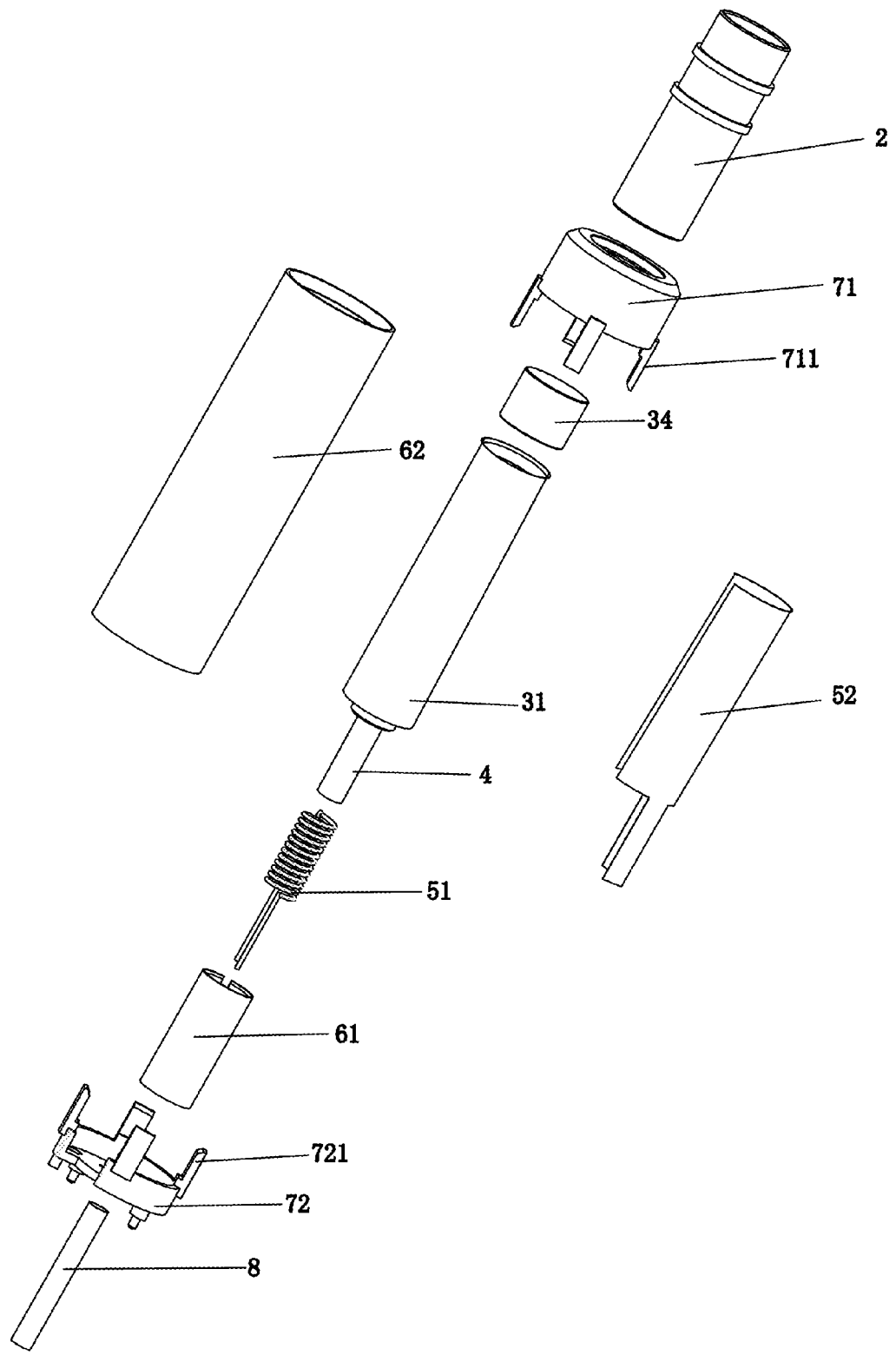
FIG. 6 is a partial structural view of a composite heating type flue-curing device provided by a third embodiment of the present application.

As shown in FIG. 5 and FIG. 6, the heat generating assembly 5 comprises a first heat generating member 51 sleeved outside the airflow heating pipe 4, and a second heat generating member 52 sleeved outside the first heating barrel 31; the first heat generating member 51 is configured to heat air inside the airflow heating pipe 4 that is to flow to the cigarette, and the second heat generating member 52 is configured to directly heat the first heating barrel 31 to heat another portion of the outer peripheral wall of the cigarette, so as to achieve a composite heating of the cigarette.

Fourth Embodiment

Figure 7:
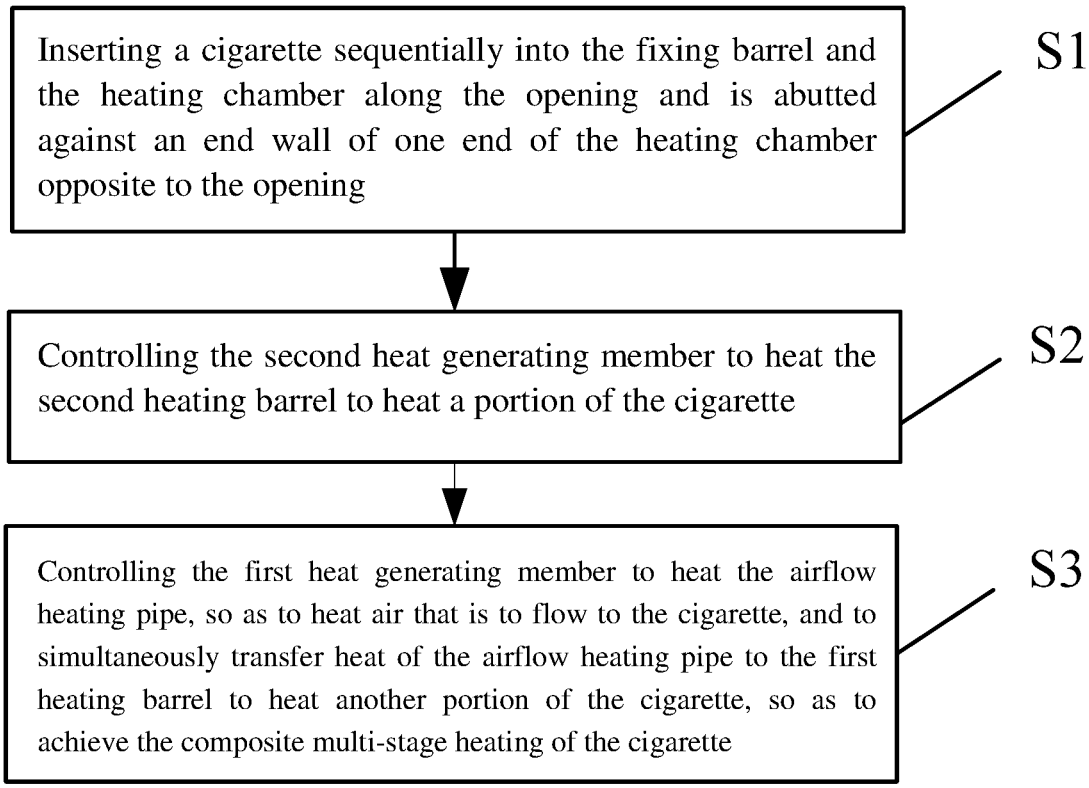
FIG. 7 is a flow chart of a composite heating method according to a fourth embodiment of the present application.

As shown in FIG. 7, the present embodiment provides a composite heating method using the composite heating type flue-curing device in the first embodiment, comprising following steps:

S1. inserting a cigarette sequentially into the fixing barrel 2 and the heating chamber 3 along the opening 11 and is abutted against an end wall of one end of the heating chamber 3 opposite to the opening 11;

S2. controlling the second heat generating member 52 to heat the second heating barrel 32 to heat a portion of the cigarette;

S3. controlling the first heat generating member 51 to heat the airflow heating pipe 4, so as to heat air that is to flow to the cigarette, and to simultaneously transfer heat of the airflow heating pipe 4 to the first heating barrel 31 to heat another portion of the cigarette, so as to achieve the composite multi-stage heating of the cigarette.

Typically, the first heat generating member 51 and the second heat generating assembly 52 may be set to a same temperature or may be set to different temperatures to meet the diversified requirements of customers.

The composite heating method in the embodiment can firstly control a portion of the heat generating assembly to heat a portion of the cigarette, and when the portion of the cigarette is fully evaporated, an air heating is activated to evaporate the remaining cigarette, so as to solve the problem that the cigarette evaporation is insufficient or the evaporation is too fast.

Fifth Embodiment

Figure 8:
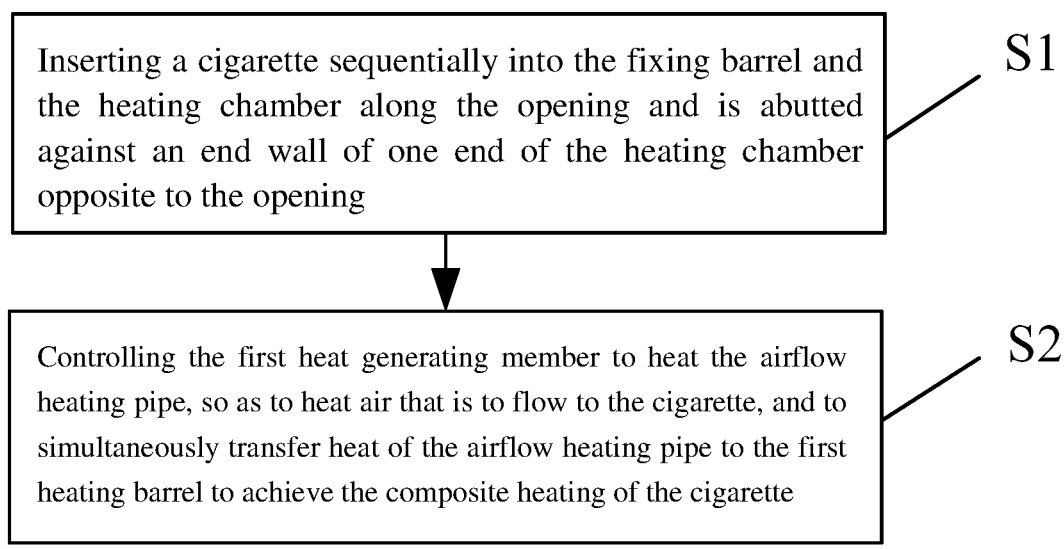
FIG. 8 is a flow chart of a composite heating method according to a fifth embodiment of the present application.

As shown in FIG. 8, the present embodiment provides a composite heating method using the composite heating type flue-curing device in the second embodiment, comprising following steps:

S1. inserting a cigarette sequentially into the fixing barrel 2 and the heating chamber 3 along the opening 11 and is abutted against an end wall of one end of the heating chamber 3 opposite to the opening 11;

S2. controlling the first heat generating member 51 to heat the airflow heating pipe 4, so as to heat air that is to flow to the cigarette, and to simultaneously transfer heat of the airflow heating pipe 4 to the first heating barrel 31 to achieve the composite heating of the cigarette.

The composite heating method in this embodiment is capable of heating air that is about to enter the cigarette, transferring the heat to the first heating barrel 31, and simultaneously heating an outer peripheral wall of the cigarette, so as to solve the problem of insufficient evaporation of the cigarette.

Sixth Embodiment

Figure 9:
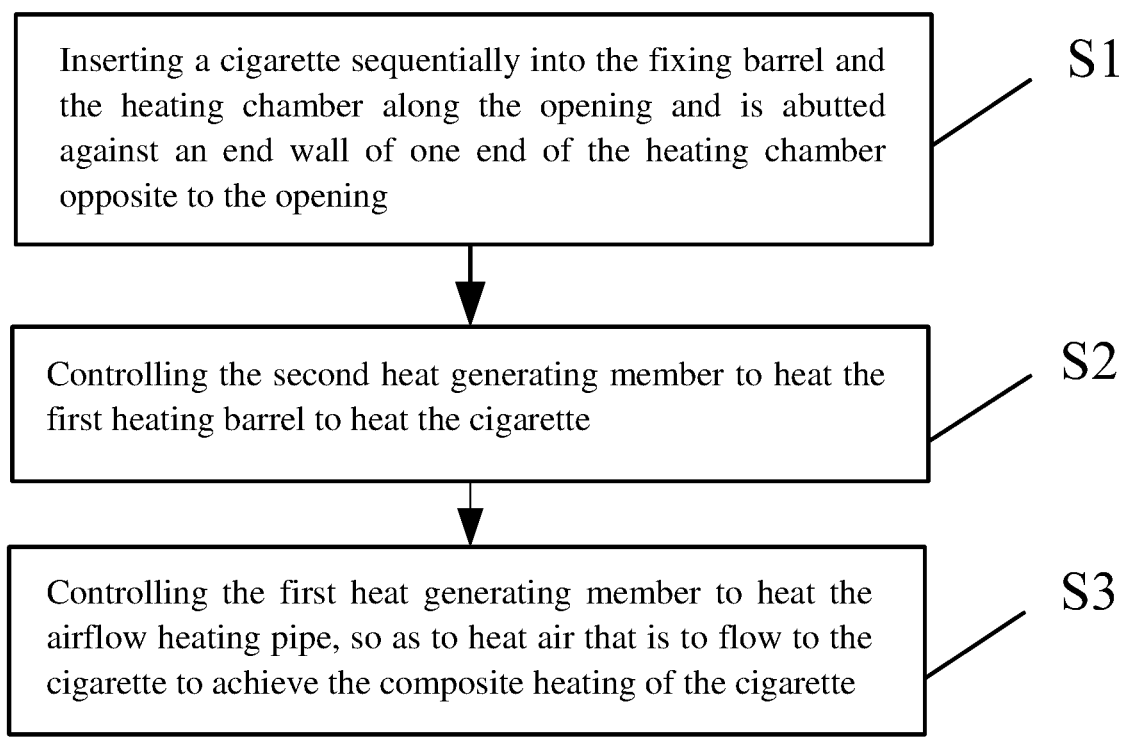
FIG. 9 is a flow chart of a composite heating method according to a sixth embodiment of the present application.

As shown in FIG. 9, the present embodiment provides a composite heating method using the composite heating type flue-curing device in the third embodiment, comprising following steps:

S1. inserting a cigarette sequentially into the fixing barrel 2 and the heating chamber 3 along the opening 11 and is abutted against an end wall of one end of the heating chamber 3 opposite to the opening 11;

S2. controlling the second heat generating member 52 to heat the first heating barrel 31 to heat the cigarette;

S3. controlling the first heat generating member 51 to heat the airflow heating pipe 4, so as to heat air that is to flow to the cigarette to achieve the composite heating of the cigarette.

Typically, the first heat generating member 51 and the second heat generating assembly 52 may be set to the same temperature or may be set to different temperatures to meet the diversified requirements of customers.

The composite heating method in the embodiment can firstly control a portion of the heat generating assembly to heat a portion of the cigarette, and when the portion of the cigarette is fully evaporated, an air heating is activated to evaporate the remaining cigarette, so as to solve the problem that the cigarette evaporation is insufficient or the evaporation is too fast.

In summary, one or more technical solutions provided in the embodiments of the present application have at least the following technical effects or advantages: firstly, a portion of the heat generating assembly can be controlled to heat a portion of the cigarette, and when the portion of the cigarette is fully evaporated, an air heating is activated to evaporate the remaining cigarette, so as to solve the problem that the cigarette evaporation is insufficient or the evaporation is too fast, and satisfying a user's habit of smoking for a long time.

While the present application has been described typical embodiments of the present application, those skilled in the art can make additional changes and modifications to the embodiments as long as they know the creative conception of the present application. Therefore, the appended claims are intended to be interpreted as including the typical embodiments and other additions and modifications within a range of the present application.

It will be apparent that those skilled in the art can make various modifications and variations to the present application without departing from the spirit and scope of the present application. Thus, it is intended that the present application comprises such modifications and variations as the modifications and variations are within the scope of the appended claims and technical solutions which is equaled or similar to the appended claims.

The invention claimed is:

1. A composite heating type flue-curing device wherein comprising a case (1), one end of the case (1) is provided with an opening (11), and a fixing barrel (2) communicated with the opening (11) is defined in an inner portion of the case (1), one end of the fixing barrel (2) which is opposite to the opening (11) is sequentially provided with a heating chamber (3) and an airflow heating pipe (4) which are communicated with each other, and the airflow heating pipe (4) is formed by radially shrinking the heating chamber (3) in a direction opposite to the opening (11); wherein one end of a cigarette is sequentially inserted into the fixing barrel (2) and the heating chamber (3) along the opening (11) and is abutted against an end wall of one end of the heating chamber (3) which is opposite to the opening (11), the other end of the cigarette extends outside the case (1) from the opening (11) for a user to inhale; and wherein the airflow heating pipe (4) is sleeved by a heat generating assembly (5), the heat generating assembly (5) is configured to heat air that is to flow to the cigarette from an inner portion of the airflow heating pipe (4), and to simultaneously transfer heat to the heating chamber (3) to heat an outer peripheral wall of the cigarette; or the airflow heating pipe (4) and the heating chamber (3) are both sleeved by the heat generating assembly (5), the heat generating assembly (5) is configured to simultaneously heat the heating chamber (3) and the airflow heating pipe (4) to achieve a composite heating of the cigarette;

wherein the heating chamber (3) comprises a first heating barrel (31) and at least one second heating barrel (32) defined between the first heating barrel (31) and the fixing barrel (2), the airflow heating pipe (4) is formed by radially shrinking the first heating barrel (31) in a direction opposite to the opening (11); and wherein the heating chamber (3) further comprises a first connecting barrel (33) connected between the first heating barrel (31) and the second heating barrel (32), and a second connecting barrel (34) connected between the second heating barrel (32) and the fixing barrel (2);

wherein the first heating barrel (31) is defined on an inner peripheral wall of one end of a first limiting step (311) near the second heating barrel (32), a second limiting step (321) is defined on an inner peripheral wall of one end of the second heating barrel (32) near the first heating barrel (31), and outer walls of two ends of the first connecting barrel (33) are abutted against the first limiting step (311) and the second limiting step (321) to space and connect the first heating barrel (31) and the second heating barrel (32).

2. The composite heating type flue-curing device according to claim 1, wherein the heat generating assembly (5) comprises a first heat generating member (51) sleeved outside the airflow heating pipe (4) and a second heat generating member (52) sleeved outside the second heating barrel (32); and wherein the first heat generating member (51) is configured to heat air inside the airflow heating pipe (4) that is to flow to the cigarette, and to simultaneously transfer heat to the first heating barrel (31) to heat a portion of the outer peripheral wall of the cigarette, and the second heat generating member (52) is configured to heat the second heating barrel (32) to heat another portion of the outer peripheral wall of the cigarette, so as to achieve a composite multi-stage heating of the cigarette.

3. The composite heating type flue-curing device according to claim 1, wherein the heating chamber (3) comprises a first heating barrel (31) and a second connecting barrel (34) which is defined between the first heating barrel (31) and the fixing barrel (2), the airflow heating pipe (4) is formed by radially shrinking the first heating barrel (31) in a direction opposite to the opening (11).

4. The composite heating type flue-curing device according to claim 3, wherein the heat generating assembly (5) comprises a first heat generating member (51) sleeved outside the airflow heating pipe (4); and wherein the first heat generating member (51) is configured to heat air inside the airflow heating pipe (4) that is to flow to the cigarette, and to simultaneously transfer heat to the first heating barrel (31) to heat a portion of the outer peripheral wall of the cigarette, so as to achieve a composite heating of the cigarette.

5. The composite heating type flue-curing device according to claim 3, wherein the heat generating assembly (5) comprises a first heat generating member (51) sleeved outside the airflow heating pipe (4), and a second heat generating member (52) sleeved outside the first heating barrel (31); and wherein the first heat generating member (51) is configured to heat air inside the airflow heating pipe (4) that is to flow to the cigarette, and the second heat generating member (52) is configured to directly heat the first heating barrel (31) to directly heat another portion of the outer peripheral wall of the cigarette, so as to achieve a composite heating of the cigarette.

6. The composite heating type flue-curing device according to claim 1, wherein a first thermal insulating barrel (61) is sleeved outside the first heat generating member (51) at a space, a first fixing bracket (71) is sleeved on an outer wall of one end of the fixing barrel (2) near the heating chamber (3), and the first fixing bracket (71) partially extends toward the heating chamber (3) to form a plurality of first clamping arms (711), a second thermal insulating barrel (62) is clamped in the plurality of first clamping arms (711), so that the second thermal insulating barrel (62) is sleeved outside the heat generating assembly (5), the heating chamber (3) and the first thermal insulating barrel (61) at a space; wherein a second fixing bracket (72) is defined at one end of the second thermal insulating barrel (62) opposite to the first fixing bracket (71), and the second fixing bracket (72) partially extends toward the heating chamber (3) to form a plurality of second clamping arms (721), the plurality of the second clamping arm (721) clamp on an outer wall of one end of the second insulating barrel (62) opposite to the first fixing bracket (71); and wherein one end of the first thermal insulating barrel (61) abuts against an outer end wall of the heating chamber (3) which is opposite to the opening (11), and the other end of the first thermal insulating barrel (61) abuts against an inner end wall of the second fixing bracket (72), the inner end wall of the second fixing bracket (72) faces the opening (11).

7. The composite heating type flue-curing device according to claim 6, wherein a through hole (722) is drilled at a center of the second fixing bracket (72), and an air intake pipe (8) passes through the through hole (722) to connect to the airflow heating pipe (4); and wherein a first thermal insulating space (63) is formed between the first thermal insulating barrel (61) and the first heat generating member (51); the first fixing bracket (71), the second thermal insulating barrel (62) and the second fixing bracket (72) are enclosed to form a thermal insulating case; a second insulated space (64) is formed among the heat generating assembly (5), the heating chamber (3) and the first thermal insulating barrel (61) which are defined in the thermal insulating case.

8. The composite heating type flue-curing device according to claim 7, wherein a bottom cover (12) is detachably provided at one end of the case (1) opposite to the opening (11), and a first air inlet hole (121) is defined on the bottom cover (12) to allow air to enter an inner portion of the case (1); and wherein a fixing member (9) is defined between the bottom cover (12) and the second fixing bracket (72), and the fixing member (9) is provided with a second air inlet hole (91), and an end of the air intake pipe (8) opposite to the opening (11) extends outside the through hole (722) and is inserted into the second air inlet hole (91), the first air inlet hole (121), the second air inlet hole (91), the air intake pipe (8) and the airflow heating pipe (4) are sequentially communicated to form an air intake passage (S1).

9. The composite heating type flue-curing device according to claim 8, wherein the airflow heating pipe (4) and the first heating barrel (31) are both made of a thermal conduction material; the second connecting barrel (34), the first insulating barrel (61), the second insulating barrel (62), the first fixing bracket (71), the second fixing bracket (72), and the fixing barrel (2) are all made of a thermal insulation material.

10. A composite heating method using the composite heating type flue-curing device of claim 2, wherein comprising following steps: S1. inserting a cigarette sequentially into the fixing barrel (2) and the heating chamber (3) along the opening (11) and is abutted against an end wall of one end of the heating chamber (3) opposite to the opening (11); S2. controlling the second heat generating member (52) to heat the second heating barrel (32) to heat a portion of the cigarette; S3. controlling the first heat generating member (51) to heat the airflow heating pipe (4), so as to heat air that is to flow to the cigarette, and to simultaneously transfer heat of the airflow heating pipe (4) to the first heating barrel (31) to heat another portion of the cigarette, so as to achieve the composite multi-stage heating of the cigarette.

\* \* \* \* \*